(12) United States Patent
Feger et al.

(10) Patent No.: US 6,465,428 B1
(45) Date of Patent: Oct. 15, 2002

(54) PHARMACEUTICAL COMBINATIONS BASED ON DALFOPRISTINE AND QUINUPRISTINE, AND ON CEFEPIME

(75) Inventors: Celine Feger, Paris (FR); Harriette Nadler, Downingtown, PA (US); Philippe Moreillon, Lausanne (CH)

(73) Assignee: Aventis Pharma S.A., Antony (FR)

( * ) Notice: Subject to any disclaimer, the term of this patent is extended or adjusted under 35 U.S.C. 154(b) by 0 days.

(21) Appl. No.: 09/645,563

(22) Filed: Aug. 25, 2000

Related U.S. Application Data

(60) Provisional application No. 60/151,079, filed on Aug. 27, 1999.

(51) Int. Cl.$^7$ .................. A61K 31/421; A61K 31/546; A61K 38/12
(52) U.S. Cl. .................. 514/11; 514/9; 514/202; 514/374
(58) Field of Search ................ 514/9, 11, 16, 514/17, 202, 374; 530/317, 329; 540/222, 456; 548/218, 325

(56) References Cited

PUBLICATIONS

J. Vouillamoz et al., "Synercid (SYN) Alone or Combined with Cefepime (FEP) in the Treatment (Rx) of Experimental Endocarditis (EE) Due to Methicillin–Resistant *Staphylococcus aureaus* (MRSA) Resistant to Macrolide–Lincosamide– Streptogramin B ($MLS_B$–R)," ICAAC Session 214–B, Paper B–76 (Sep. 24–27, 1998).

*Primary Examiner*—Jeffrey E. Russel
(74) *Attorney, Agent, or Firm*—Finnegan, Henderson, Farabow, Garrett & Dunner LLP

(57) ABSTRACT

The present invention relates to pharmaceutical combinations of group A and group B streptogramins, in particular to combinations of dalfopristine and quinupristine, with cefepime, which combinations can exhibit a synergism of antibiotic action, to pharmaceutical compositions comprising the active ingredients, and to the bactericidal and bacteriostatic use of the combinations and compositions.

62 Claims, 2 Drawing Sheets

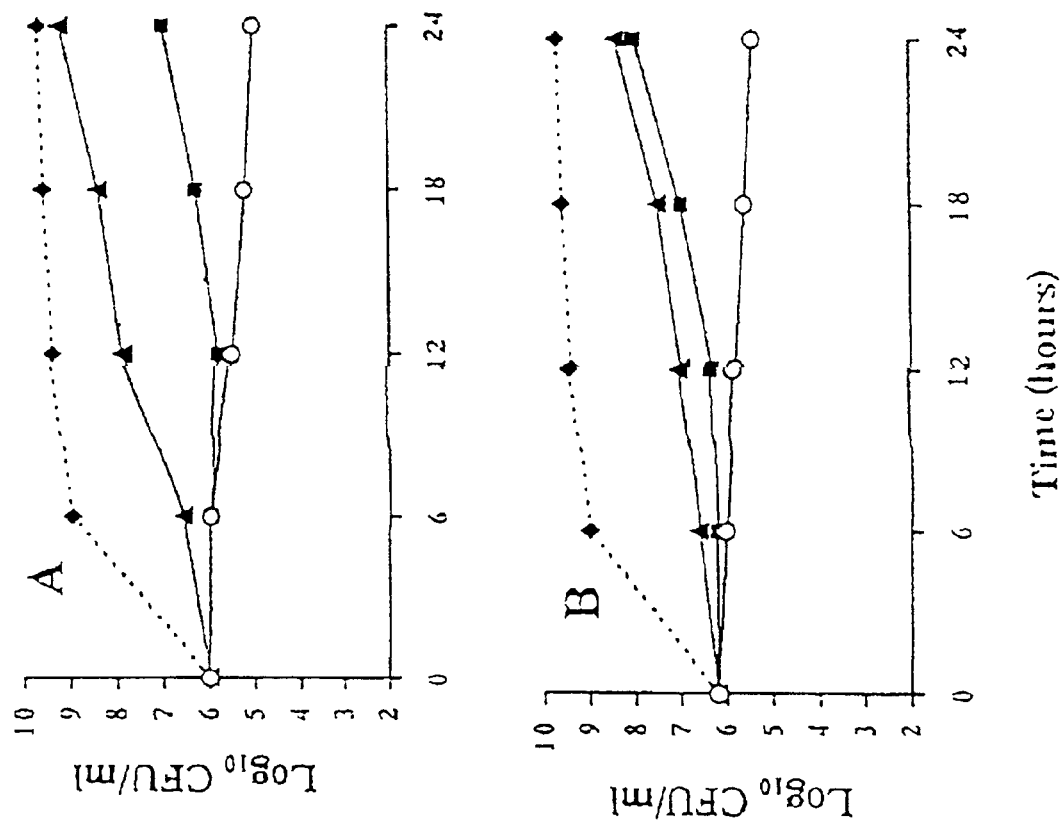
Figure 2 (Time-kill experiments) low drug serum levels

PHARMACEUTICAL COMBINATIONS BASED ON DALFOPRISTINE AND QUINUPRISTINE, AND ON CEFEPIME

This application claims priority benefit of U.S. Provisional Application No. 60/151,079, filed Aug. 27, 1999.

The present invention relates to combinations of quinupristine and dalfopristine with cefepime, which combinations can exhibit a synergism of action including bacteriostatic, as well as bactericidal, activity.

The present invention also relates to injectable pharmaceutical compositions intended for parenteral administration, which compositions comprise quinupristine and dalfopristine, in combination with cefepime.

European patent application EP 248,703, the disclosure of which is specifically incorporated by reference herein, describes streptogramin derivatives of group B of general formula:

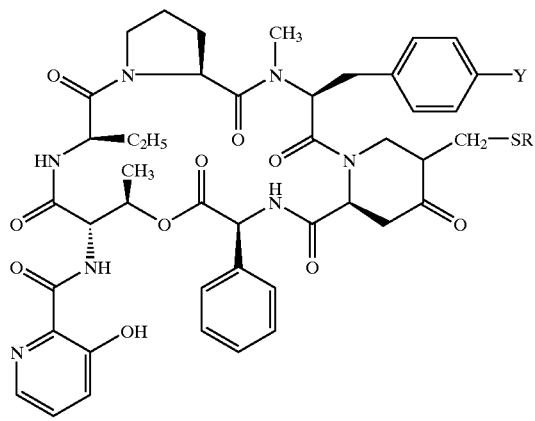

as well as their combinations with streptogramin derivatives of group A of the general structure:

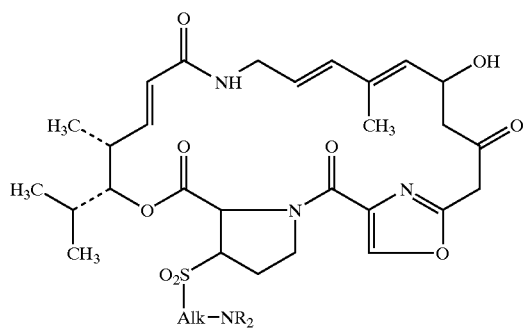

Streptogramin derivatives of group A are described in more detail in European patent no. EP 191,662, the disclosure of which is specifically incorporated by reference herein.

Quinupristine, a derivative of pristinamycin I (a group B streptogramin), and dalfopristine, a derivative of pristinamycin II (a group A streptogramin), are the components of Synercid®:

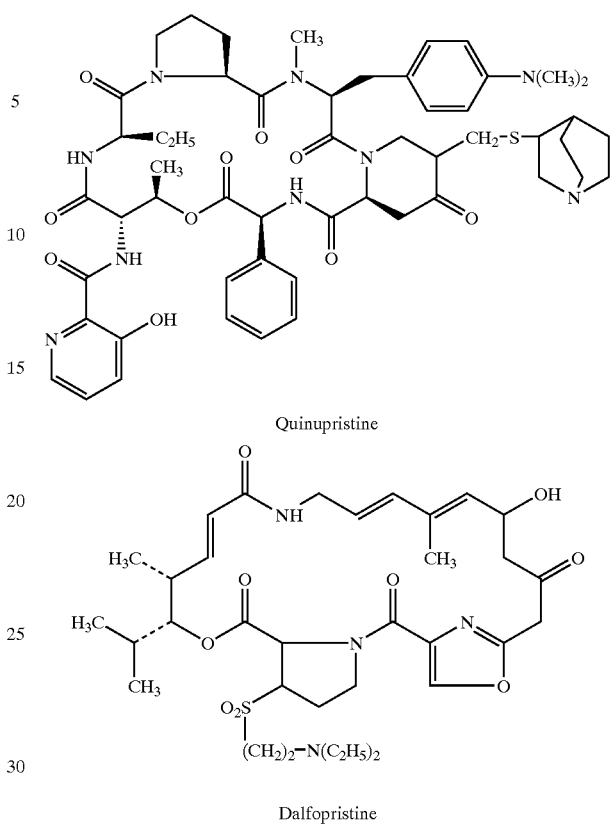

Quinupristine

Dalfopristine

Synercid® (quinupristine/dalfopristine) is an injectable 30/70 combination potent against most gram-positive pathogens, including methicillin resistant *Staphylococcus aureus* (MRSA) and vancomycin-resistant *Enterococcus faecium* (VREF). Its antibacterial activity is cited in many publications, including The Annals of Pharmacotherapy, 29, 1022–1026 (1995); Microbial Drug Resistance, 1, 223–234 (1995); and Antimicrobial Agents Chemother., 39, 1419–1424 (1995); etc.

International patent application WO 98/22107, the disclosure of which is specifically incorporated by reference herein, describes the preparation of stabilized pharmaceutical compositions comprising a quinupristine/dalfopristine combination, achieved in salt form, by adding at least stoichiometric amounts of methanesulphonic acid or of hydrochloric acid, and at a pH within the range of 3.5 to 5.0.

In the clinical environment, some bacteria, MRSA for instance, may jeopardize the efficacy of quinupristine/dalfopristine if adequate concentrations of dalfopristine are not present at the infection site. One way of circumventing this problem has been by increasing the number of doses of quinupristine/dalfopristine within a 24-hr period, or using a system of continuous infusion.

Cefepime is a compound of the class of β-lactams of the cephalosporin related structure: (6R,7R)-7-(2-(2-aminothiazol-4-yl)-2(Z)-(methoxyimino)acetamido)-3-(1-methyl-pyrrolidiniomethyl)-3-cephem-4-carboxylate [Drugs of the Future, 10(10), 805 (1985), the disclosure of which is specifically incorporated by reference herein], which is usually administered by injection in patients with moderate to severe infections.

It has now been found, and this forms the subject of the present invention, that the combination of quinupristine/dalfopristine with cefepime can be of high interest in the treatment of difficult-to-treat or life-threatening infections that require rapid bactericidal activity, as such combination can exhibit a synergy of action against such bacteria. The synergy results in a much higher potency which can, for instance, allow a decrease of the concentration of quinupristine/dalfopristine for administration or widen the dosing interval necessary to inhibit and to kill said bacteria, in particular against multi-drug resistant staphylococci, including methicillin-resistant strains.

Both in vitro and in vivo animal studies have been carried out and results of each confirm the other.

The experimental studies have been carried out in rats with experimental multi-resistant MRSA Endocarditis.

BRIEF DESCRIPTION OF THE DRAWINGS

FIG. 2 shows time-kill experiments using quinupristine/dalfopristine or cefepime alone or combined together.

EXPERIMENTS

Figure 1:
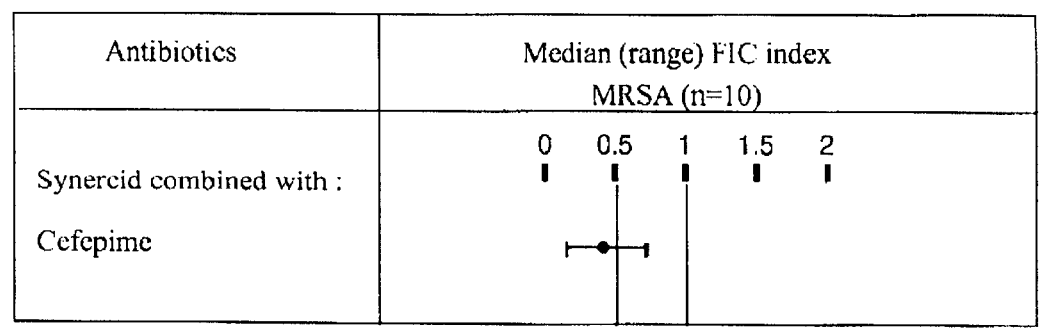
FIG. 1 shows the synergism of Synercid combined with cefepime.

Material and Methods
Microorganisms and Growth Conditions:

A panel of 10 clinical isolates of MRSA (5 $MLS_B$-susceptible (susceptible to Macrolide-Lincosamide-Streptogramin B) and 5 C-$MLS_B$-resistant (Constitutively Resistant to Macrolide-Lincosamide-Streptogramin B)) originating from various geographical areas were tested for their susceptibilities to quinupristin/dalfopristin and to cefepime. Two of these isolates, namely AW7 and P8, were further used for animal experiments. These both were C-$MLS_B$-resistant.

Bacteria were grown at 35° C., either in liquid cultures in tryptic soy broth (TSB; Difco Laboratories, Detroit, Mich.) or cation supplemented Mueller Hinton Broth (MHB; Difco), or on tryptic soy agar (TSA; Difco). All growth media were supplemented with 2% of sodium chloride to increase the expression of β-lactam resistance by MRSA. Bacterial stocks were kept at −70° C. in TSB, supplemented with 10% (vol/vol) glycerol.

The MIC (minimum inhibitory concentration) of the tested antibiotics was determined by a known broth macrodilution method (D. Amsterdam, Susceptibility testing of antimicrobials in liquid media, p.52–111, In V. Lorian ed., Antibiotics in Laboratory Medicine, Williams and Wilkins, Baltimore (1996)) with final inoculum of $10^5$ to $10^6$ CFU/ml. The MIC was defined as the lowest antibiotic concentration that inhibited visible bacterial growth after 24 hours of incubation at 35° C.

Antibiotic interactions were assessed by the checkerboard method, as described by G. M. Eliopoulos and R. C. Jr. Mollering, Antimicrobial combinations, p.330–396, In V. Lorian ed., Antibiotics in Laboratory Medicine, Williams and Wilkins, Baltimore (1996). 96-well microtiter plates (Dynatech Microtiter, Vg.) were filled with MHB containing 2 fold increasing concentrations of the partner antibiotic tested (cefepime) in the vertical rows. The plates were inoculated with a final inoculum of $10^5$ CFU/ml per well from a logarithmic-phase culture, and incubated for 18 hours at 35° C. before visible bacterial growth was observed. The Fractional Inhibitory Concentration Index (FIC index) between the 2 antibiotics was defined as the most favorable point of the drug combination. The FIC index was determined by the formula: $[Q-D]/[MIC_{Q-D}]+[\text{cefepime}]/[MIC_{cefepime}]$=FIC index, where [Q-D] and [cefepime] are the lowest inhibitory concentrations of these 2 antibiotics in a given row of microtiter plate, and $[MIC_{Q-D}]$ and $[MIC_{cefepime}]$ are the standard MICs of the drugs for the test organism. FIC indexes were interpreted as follows: FIC indexes ≦0.5 correspond to synergism; FIC indexes between 0.5 and 1 correspond to an additive effect.

For time-kill curves, series of flasks containing fresh prewarmed medium were inoculated with $10^6$ CFU/ml (final concentration) from an overnight culture of bacteria, and the bacteria were further incubated at 35° C. with aeration at 120 rpm in a shaking incubator. Immediately after incubation, antibiotics were added to the flasks at final concentrations approximating the low levels of antibiotics produced in the serum of humans and rats by therapeutic doses of the drugs. Viable counts were determined just before and at various times after the addition of the antibiotics by plating adequate dilutions of the cultures on agar plates. To avoid antibiotic carryover, 0.5 ml samples of the structures were transferred from the flasks into microcentrifuge tubes, and the bacteria were spun and resuspended twice in antibiotic-free medium to remove residual drugs. Then the bacterial suspensions were serially diluted and spread on agar plates. When the β-lactam drug (cefepime) was tested, the plates were supplemented with penicillinase as an additionnal precaution to avoid antibiotic carryover. Finally, due to the prolonged post antibiotic effect of quinupristine/dalfopristine, it was important to incubate the plates for at least 48 hours before the determination of viable counts. This avoided the false impression of quinupristine/dalfopristine-induced killing due to the delayed growth of surviving bacteria on the plate.
Production of Endocarditis:

Sterile aortic vegetations were produced in female Wistar rats (weight 180 to 200 g) by the method of Heraiefet al., Infect Immunol., 37, 127–31 (1982), the disclosure of which is incorporated herein by reference in its entirety. Close by, an intravenous line containing a Silastic catheter was inserted into the jugular vein of a rat. The distal portion of the catheter was connected to a programmable pump device through a swivel, thus allowing the animals to move around their cage. The pump was set to deliver a volume of 0.2 ml of saline per hour to keep the line open until the onset of the therapy. In some experiments, quinupristine/dalfopristine was injected in combination with cefepime to the animals, with 2 infusion pumps, one to simulate human kinetics of quinupristine/dalfopristine and one to simulate human kinetics of cefepime. The 2 pumps were connected to a 2 way swivel and the drugs were infused into the animals via 2 independent jugular lines. No i.v. lines were placed in the control animals. Bacterial endocarditis was induced 24 hours after catheterization of the animals with 0.5 ml of saline containing $10^5$ CFU of either of the test organisms. This inoculum was 10 times larger than the minimum inoculum producing endocarditis in 90% of the untreated rats.
Therapy for Experimental Endocarditis:

Treatment was started 12 hours after bacterial challenge and lasted 3 or 5 days. The distribution of the antibiotics simulated the drug kinetics in the serum of humans. Quinupristine/dalfopristine was given to simulate treatment in humans with 7 mg/kg of the drug administered i.v. every 12 hours. Cefepime was given to simulate treatment in humans with 2 g of the drug given i.v. every 12 hours. This required, for the experiment, a total amount (mg/kg of body weight) per 12 hours of 38 mg/kg of quinupristine/dalfopristine and 142 mg/kg of cefepime.
Evaluation of Infection:

The control rats were sacrificed at the onset of the treatment (i.e., 12 hours after inoculation) in order to measure both the frequency and the severity of valvular infection at the start of the therapy. Treated rats were sacrificed 12 hours after the low level of the last antibiotic dose of either test drug. At that time, no residual antibiotic could be detected in the blood. The valvular vegetation were dissected under sterile conditions, weighed, homogenized in 1 ml of saline, and serially diluted before being plated for colony counts. The number of colonies growing on the plates was determined after 48 hours of incubation at 35° C. Bacterial densities in the vegetations were expressed as $\log_{10}$ CFU/g of tissue. The minimum detection level was $\geq 2$ $\log_{10}$ CFU/g of vegetation. For statistical comparisons of differences between the vegetation bacterial densities of various treatment groups, culture-negative vegetations were considered to contain 2 $\log_{10}$ CFU/g.

RESULTS

FIC Indexes of Quinupristine/dalfopristine Combined with Cefepime

Table 1 presents the ranges of MICs of the antibiotics for 10 MRSA isolates that were used to determine the FIC indexes. The FIC indexes demonstrated a positive interaction between quinupristine/dalfopristine and cefepime on MRSA isolates.

FIG. 1: synergism corresponds to FIC indexes $\geq 0.5$; addition corresponds to FIC indexes between 0.5 and 1.

TABLE 1

Ranges of MICs of the antibiotics for $MLS_B$-susceptible (susceptible to Macrolide Lincosanside-Streptogramin B - $MLS_B$-S) and constitutively $MLS_B$-resistant (Constitutively Resistant to Macrolide-Lincosamide-Streptogramin B-macrolide- and lincosamide-resistarit or C-$MLS_B$-R) Staphylococcus aureus isolates also resistant to methicillin (MRSA *)

| Antibiotics | Range of MICs (mg/l) | |
|---|---|---|
| | MRSA $MLS_B$-S | MRSA C-$MLS_B$-R |
| Quinupristine/dalfopristine | 0.25 | 0.25–0.5 |
| cefepime | >64 | >64 |

\* MRSA included 5 $MLS_B$-susceptible and 5 C-$MLS_B$-resistant clinical isolates Time kill experiments with MRSA AW7 and MRSA P8 were performed with concentrations mimicking low antibiotic levels obtained during i.v. treatment in humans or in rats.

Both MRSA AW7 and MRSA P8 were first exposed to quinupristine/dalfopristine or cefepime alone or combined together (FIG. 2, A and B). The drugs used alone were ineffective and failed to prevent bacteria growth. In contrast, when combined together, quinupristine/dalfopristine and cefepime blocked bacterial growth and even inflicted a reproducible loss of viability of 1–2 $\log_{10}$ CFU/ml after 24 hours of drug exposure. FIG. 2 shows time-kill experiments with AW7 (A) and P8 (B) exposed to concentrations of quinupristine/dalfopristine and/or cefepime, mimicking low antibiotic levels obtained during i.v. treatment in humans or in rats. Cultures received either no drug (diamonds), quinupristine/dalfopristine alone (squares), cefepime alone (triangles) or the combination of quinupristine/dalfopristine and cefepime (open circles). Low concentrations of quinupristine/dalfopristine and cefepime were 0.5 mg/l and 5 mg/l respectively.

Efficacy of Quinupristine/dalfopristine Alone or Combined with Cefepime in the Treatment of Experimental Endocarditis in Rats It is generally agreed that endocarditis models are relatively good indicators of bactericidal activity. Antibiotics with bactericidal properties or antibiotic combinations with synergistic effects allowing a bactericidal activity of the combination are recommended in life-threatening infections when rapid antibacterial activity is required or in difficult-to-treat infections.

The C-$MLS_B$ resistant MRSA: AW7 and P8, respectively, were tested further in animal studies. For these organisms, the MIC of quinupristine/dalfopristine was 0.5 mg/l and the MIC of cefepime was 64 mg/l.

For the model to be able to demonstrate synergy, in terms of bactericidal activity, when the drugs were to be combined, quinupristine/dalfopristine was given only at low doses (equivalent to 7.5 mg/kg i.v. every 12 hours (programmable pump)), in order to fail in monotherapy vs. the multi-resistant MRSA. Cefepime was given at 2 g i.v. every 12 hours.

Surprisingly, whereas monotherapy on C-$MLS_B$ resistant MRSA AW7 and P8 failed, in contrast, the combination gave a significant 5–6 log 10 decrease in the vegetation bacteria titers (p<0.05) after 5 days with the combination of quinupristine/dalfopristine and cefepime, when compared to both animals receiving single therapy and untreated controls.

Results were: (infected rats/total rats (median $\log_{10}$ CFU/g of vegetation))

| Treatment | Strain AW-7 | Strain P8 |
|---|---|---|
| Controls | 6/8 (7.9) | 8/8 (7.9) |
| Synercid ® BID | 8/8 (9.1) | 7/7 (9.1) |
| cefepime BID | 6/6 (8.6) | 8/8 (9.0) |
| Synercid ®/cefepime combination | 5/13 (2.0)* | 8/13 (3.6)** |

\*P < 0.05 compared to all groups; \*\*P < 0.05 compared to each drug used alone Therefore, as demonstrated, the treatment with such a combination allowed use of lower dose(s) of the associated drugs or wider intervals between dosing with better efficacy (bacteriostatic and bactericidal) than achievable using an antibiotic monotherapy.

The doses of active principle (Synercid®: quinupristine+ dalfopristine association) that can be administered to patients range between 5 and 15 mg/kg, and are typically within the range of from 5 to 7.5 mg/kg every 8 hours.

The dose of cefepime usually administered to patients for moderate to severe infections is approximately 2 g i.v. every 12 hours.

In the above mentioned combinations, quinupristine/ dalfopristine and cefepime can interestingly be used for treatment of humans in continuous injection or with shortened intervals between administrations. The doses of quinupristine/dalfopristine can be chosen in the range of from 10 to 30 or 60 mg/kg daily, in fractionated doses or continuous injection, and the doses of cefepime can be chosen in the range of from 1 to 4 or 8 g daily, in fractionated doses or continuous injection.

It is understood that the inventive combination can be used in accordance with several types of administrations, such as coadministration at the same time or different times, and administration via multilumen catheters.

For the disclosed treatment, formulations of the quinupristine/dalfopristine can be presented in liquid, lyophilized or frozen form.

The lyophilized formulations can be taken up, at the time of use, in water for injectable preparations (water fip) or in any compatible injectable medium, in particular in media such as glucose solutions (aqueous 5% glucose solution for example), or, without any limitation being implied, with dextran solutions, polyvinylpyrrolidone solutions or polysorbate 80 solutions. According to a preferred method, the formulations are taken up in solution by passing via a concentrated solution, for example, of 50 to 250 mg/ml, and more typically about 100 mg/ml, referred to herein below as the "concentrate"; this solution is diluted at the time of use in an injectable medium as described above for an administration by infusion; it is also possible to take up the lyophilizate in water fip and then to dilute the concentrate thus obtained in the desired injectable medium.

The frozen formulations can be frozen from solutions initially prepared (from 5 to 250 mg/ml) or from diluted solutions (for the preparation of frozen bags, for example). They are thawed at the time of use and then diluted, if necessary. The solutions presented in the liquid state can contain from 5 to 250 mg/ml of active principle. They are diluted at the time of use to concentrations of between 0.5 and 10 mg/ml.

According to the invention, the formulations or compositions of quinupristine/dalfopristine, optionally reconstituted in the form of a concentrated solution (concentrate) or diluted, can be combined for coadministration with the cefepime solution at the time of injection. The combination can be made using 2 infusion bags, one containing quinupristine/dalfopristine in the injectable medium and the other containing the cefepime solution also in the injectable medium or using 2 syringes, one containing quinupristine/dalfopristine in the injectable medium, and the other containing the cefepime solution, or alternatively the combination can be made using one of the drugs in an infusion bag and the other in a syringe.

It is understood that the presentation kits for the formulation of quinupristine/dalfopristine and for the cefepime composition also fall within the context of the present invention. Presentation kits of any form can be suitable, in particular, for example, for presentations in the form of a twin-bottle, presentations in the form of an infusion bag containing quinupristine/dalfopristine and a bottle or an ampoule containing cefepime, presentations involving one or more bottles comprising quinupristine/dalfopristine and a bottle or an ampoule of cefepime. Devices such as two-compartment syringes may also prove to be particularly suitable.

It is understood that the present invention can be applied to other soluble streptogramin derivatives which can also be combined with cefepime. For example, the present invention can also be applied to streptogramin derivatives as described in European Patents EP 133,097, EP 135,410, EP 191,662, EP 248,703, WO 99/43699, and WO 99/05165, the disclosures of which are incorporated herein by reference, wherein a group A streptogramin component and a group B streptogramin component can be combined with cefepime.

The present invention may be embodied in other specific forms without departing from its spirit or essential characteristics. The described embodiments are to be considered in all respects as illustrative only and not restrictive. The scope of the invention is, therefore, indicated by the appended claims rather than by the foregoing description. All changes which come within the meaning and range of equivalency of the claims are to be embraced within their scope.

What is claimed is:

1. A synergistic antibiotic combination, said combination comprising a synergistically effective amount of a combination of at least one group A streptogramin and at least one group B streptogramin, and cefepime.

2. The synergistic antibiotic combination of claim 1, wherein the group A streptogramin is dalfopristine and the group B streptogramin is quinupristine.

3. A pharmaceutical composition, comprising a synergistically effective amount of a combination of at least one group A streptogramin and at least one group B streptogramin, and cefepime.

4. The pharmaceutical composition of claim 3, wherein the group A streptogramin is dalfopristine and the group B streptogramin is quinupristine.

5. A presentation kit, comprising at least two compartments, wherein a first compartment comprises a combination of at least one group A streptogramin and at least one group B streptogramin, wherein a second compartment comprises cefepime, and wherein said combination in said first compartment and said cefepime in said second compartment are present in synergistic antibiotic amounts with respect to each other.

6. The presentation kit of claim 5, wherein each of the two compartments comprises a single bottle, which together form a twin-bottle kit.

7. The presentation kit of claim 6, wherein the group A streptogramin is dalfopristine and the group B streptogramin is quinupristine.

8. The presentation kit of claim 5, wherein said first compartment is in the form of an infusion bag containing said combination of at least one group A streptogramin and at least one group B streptogramin, and said second compartment is in the form of a bottle or an ampoule containing said cefepime.

9. The presentation kit of claim 8, wherein the group A streptogramin is dalfopristine and the group B streptogramin is quinupristine.

10. The presentation kit of claim 5, wherein said first compartment is in the form of at least one bottle and said second compartment is in the form of a bottle or an ampoule.

11. The presentation kit of claim 10, wherein the group A streptogramin is dalfopristine and the group B streptogramin is quinupristine.

12. The presentation kit of claim 5, wherein said first compartment is in the form of a syringe and said second compartment is in the form of a syringe.

13. The presentation kit of claim 12, wherein the group A streptogramin is dalfopristine and the group B streptogramin is quinupristine.

14. The presentation kit of claim 5, wherein said first compartment or said second compartment contains at least one pharmaceutically acceptable carrier.

15. A method for inhibiting or killing at least one bacteria, comprising administering to a mammal in need or desire thereof an effective amount of the synergistic combination of claim 1.

16. A method for inhibiting or killing at least one bacteria, comprising administering to a mammal in need or desire thereof an effective amount of the pharmaceutical composition of claim 3.

17. The method of claim 15, wherein the bacteria comprises a multi-drug resistant staphylococci.

18. The method of claim 16, werein the bacteria comprises a multi-drug resistant staphylococci.

19. The method of claim 15, wherein the group A streptogramin is dalfopristine and the group B streptogramin is quinupristine.

20. The method of claim 16, wherein the group A streptogramin is dalfopristine and the group B streptogramin is quinupristine.

21. The method of claim 15, wherein the administration is accomplished using two infusion bags, wherein one infusion bag contains said combination of at least one group A streptogramin and at least one group B streptogramin and the second infusion bag contains said cefepime.

22. The method of claim 21, wherein the group A streptogramin is dalfopristine and the group B streptogramin is quinupristine.

23. The method of claim 16, wherein the administration is accomplished using two infusion bags, wherein one infusion bag contains said combination of at least one group A streptogramin and at least one group B streptogramin and the second infusion bag contains said cefepime.

24. The method of claim 23, wherein the group A streptogramin is dalfopristine and the group B streptogramin is quinupristine.

25. The method of claim 15, wherein the administration is accomplished using two syringes, wherein one syringe contains said combination of at least one group A streptogramin and at least one group B streptogramin and the second syringe contains said cefepime.

26. The method of claim 25, wherein the group A streptogramin is dalfopristine and the group B streptogramin is quinupristine.

27. The method of claim 16, wherein the administration is accomplished using two syringes, wherein one syringe contains said combination of at least one group A streptogramin and at least one group B streptogramin and the second syringe contains said cefepime.

28. The method of claim 27, wherein the group A streptogramin is dalfopristine and the group B streptogramin is quinupristine.

29. The method of claim 15, wherein the administration is accomplished using an infusion bag and a syringe, wherein either the infusion bag or the syringe contains said combination of at least one group A streptogramin and at least one group B streptogramin and the remaining infusion bag or syringe contains said cefepime.

30. The method of claim 29, wherein the group A streptogramin is dalfopristine and the group B streptogramin is quinupristine.

31. The method of claim 16, wherein the administration is accomplished using an infusion bag and a syringe, wherein either the infusion bag or the syringe contains said combination of at least one group A streptogramin and at least one group B streptogramin and the remaining infusion bag or syringe contains said cefepime.

32. The method of claim 31, wherein the group A streptogramin is dalfopristine and the group B streptogramin is quinupristine.

33. The method of claim 19, wherein the combination of dalfopristine and quinupristine is present in an amount ranging from 10 to 60 mg/kg/day and the cefepime is present in an amount ranging from 1 to 8 g/day.

34. The method of claim 20, wherein the combination of dalfopristine and quinupristine is present in an amount ranging from 10 to 60 mg/kg/day and the cefepime is present in an amount ranging from 1 to 8 g/day.

35. The method of claim 33, wherein the cefepime is present in an amount ranging from 1 to 4 g/day.

36. The method of claim 34, wherein the cefepime is present in an amount ranging from 1 to 4 g/day.

37. The method of claim 33, wherein the combination of dalfopristine and quinupristine is present in an amount ranging from 10 to 30 mg/kg/day and the cefepime is present in an amount ranging from 1 to 8 g/day.

38. The method of claim 34, wherein the combination of dalfopristine and quinupristine is present in an amount ranging from 10 to 30 mg/kg/day and the cefepime is present in an amount ranging from 1 to 8 g/day.

39. The method of claim 37, wherein the cefepime is present in an amount ranging from 1 to 4 g/day.

40. The method of claim 38, wherein the cefepime is present in an amount ranging from 1 to 4 g/day.

41. The method of claim 15, wherein said combination of the group A streptogramin and the group B streptogramin, and/or the cefepime are administered in fractionated doses.

42. The method of claim 16, wherein said combination of the group A streptogramin and the group B streptogramin, and/or the cefepime are administered in fractionated doses.

43. The method of claim 15, wherein said combination of the group A streptogramin and the group B streptogramin, and/or the cefepime are administered by continuous injection.

44. The method of claim 16, wherein said combination of the group A streptogramin and the group B streptogramin, and/or the cefepime are administered by continuous injection.

45. The method of claim 15, wherein said combination of the group A streptogramin and the group B streptogramin, and/or the cefepime are administered by infusion.

46. The method of claim 16, wherein said combination of the group A streptogramin and the group B streptogramin, and/or the cefepime are administered by infusion.

47. The synergistic antibiotic combination of claim 1, wherein said combination of the group A streptogramin and the group B streptogramin is present in liquid, lyophilized, or frozen form.

48. The pharmaceutical composition of claim 3, wherein said composition of the group A streptogramin and the group B streptogramin is present in liquid, lyophilized, or frozen form.

49. The presentation kit of claim 5, wherein said combination of the group A streptogramin and the group B streptogramin is present in liquid, lyophilized, or frozen form.

50. The presentation kit of claim 49, wherein the lyophilized form is taken up in water for an injectable preparation or in a compatible injectable medium.

51. The presentation kit of claim 50, wherein the compatible injectable medium is a 5% glucose solution.

52. The presentation kit of claim 49, wherein the frozen form is prepared from 5 to 250 mg/ml of said synergistic antibiotic combination or from diluted solutions of said synergistic antibiotic combination.

53. The presentation kit of claim 49, wherein the liquid form contains from 5 to 250 mg/ml of said synergistic antibiotic combination.

54. The presentation kit of claim 53, wherein the liquid form is diluted at the time of use to a concentration ranging from 0.5 to 10 mg/ml of said synergistic antibiotic combination.

55. The method of claim 17, wherein said multi-drug resistant staphylococci is methicillin-resistant.

56. The method of claim 18, wherein said multi-drug resistant staphylococci is methicillin-resistant.

57. The method of claim 19, wherein said administration comprises coadministration of said combination of dalfopristine and quinupristine and said cefepime at the same or different times.

58. The method of claim 20, wherein said administration comprises coadministration of said combination of dalfopristine and quinupristine and said cefepime at the same or different times.

59. The method of claim 19, wherein said administration is v ia at least one multilumen catheter.

60. The method of claim 20, wherein said administration is via at least one multilumen catheter.

61. The pharmaceutical composition of claim 3, further comprising at least one pharmaceutically acceptable carrier.

62. The pharmaceutical composition of claim 4, further comprising at least one pharmaceutically acceptable carrier.

* * * * *